United States Patent [19]

Römer et al.

[11] Patent Number: 4,620,938

[45] Date of Patent: Nov. 4, 1986

[54] HYDROTERPHENYLS

[75] Inventors: Michael Römer, Rodgau; Joachim Krause; Rudolf Eidenschink, both of Dieburg; Georg Weber, Erzhausen, all of Fed. Rep. of Germany

[73] Assignee: Merck Patent Gesellschaft mit beschrankter Haftung, Darmstadt, Fed. Rep. of Germany

[21] Appl. No.: 720,246

[22] Filed: Apr. 5, 1985

Related U.S. Application Data

[63] Continuation of Ser. No. 480,199, Mar. 30, 1983, abandoned.

[30] Foreign Application Priority Data

Mar. 30, 1982 [DE] Fed. Rep. of Germany ....... 3211601

[51] Int. Cl.$^4$ .................. G02F 1/13; C09K 3/34; C07C 13/28; C07C 25/18; C07C 39/17; C07C 121/64; C07C 43/21; C07C 63/49; C07C 69/96; C07C 69/773; C07C 121/75

[52] U.S. Cl. .................. 252/299.63; 252/299.5; 350/350 R; 350/350 S; 560/72; 560/73; 560/61; 560/102; 560/107; 560/1; 560/141; 585/20; 585/25; 570/129; 570/182; 568/743; 568/631; 562/492

[58] Field of Search ............ 252/299.63, 299.5; 350/350 R, 350 S; 260/465 D, 465 R; 560/73, 102, 107, 1, 141, 72, 61; 585/20, 25; 570/129, 182; 568/631, 743; 562/492

[56] References Cited

U.S. PATENT DOCUMENTS

| | | | |
|---|---|---|---|
| 4,154,697 | 5/1979 | Eidenschink et al. | 252/299.63 |
| 4,229,315 | 10/1980 | Krause et al. | 252/299.63 |
| 4,261,652 | 4/1981 | Gray et al. | 252/299.62 |
| 4,330,426 | 5/1982 | Eidenschink et al. | 252/299.63 |
| 4,340,498 | 7/1982 | Sugimori et al. | 252/299.63 |
| 4,387,039 | 6/1983 | Sugimori et al. | 252/299.63 |
| 4,405,488 | 9/1983 | Sugimori et al. | 252/299.63 |
| 4,410,445 | 10/1983 | Baur et al. | 252/299.63 |
| 4,422,951 | 12/1983 | Sugimori et al. | 252/299.63 |
| 4,439,340 | 3/1984 | Kojima et al. | 252/299.63 |
| 4,472,293 | 9/1984 | Sugimori et al. | 252/299.63 |
| 4,472,592 | 9/1984 | Takatsu et al. | 252/299.63 |
| 4,477,369 | 10/1984 | Sugimori et al. | 252/299.63 |
| 4,487,954 | 12/1984 | Sugimori et al. | 252/299.63 |
| 4,502,974 | 3/1985 | Sugimori et al. | 252/299.5 |
| 4,507,222 | 3/1985 | Inoue et al. | 252/299.63 |
| 4,526,704 | 7/1985 | Petrzilka et al. | 252/299.63 |
| 4,550,981 | 11/1985 | Petrzilka et al. | 252/299.64 |
| 4,584,120 | 4/1986 | Fujii et al. | 252/299.63 |

FOREIGN PATENT DOCUMENTS

| | | | |
|---|---|---|---|
| 19665 | 12/1980 | European Pat. Off. | 252/299.63 |
| 87102 | 8/1983 | European Pat. Off. | 252/299.63 |
| 87032 | 8/1983 | European Pat. Off. | 252/299.63 |
| 57-9742 | 1/1982 | Japan | 252/299.63 |
| 57-64645 | 4/1982 | Japan | 252/299.63 |
| 57-70839 | 5/1982 | Japan | 252/299.63 |
| 57-165326 | 10/1982 | Japan | 252/299.63 |
| 58-59930 | 4/1983 | Japan | 252/299.63 |
| 59-16853 | 1/1984 | Japan | 252/299.61 |
| 59-62547 | 4/1984 | Japan | 252/299.63 |
| 59-161348 | 9/1984 | Japan | 252/299.61 |
| 2092169 | 8/1982 | United Kingdom | 252/299.63 |

Primary Examiner—Teddy S. Gron
Attorney, Agent, or Firm—Millen & White

[57] ABSTRACT

New hydroterphenyls of formula I $$R^1-Cy-Cy-Ph-R^2 \qquad I$$

wherein $R^1$ is alkyl; $R^2$ is H, F, Cl, Br, I, OH, CN, alkyl, —O-alkyl, —COOR$^3$ or —O—CO—R$^3$; $R^3$ is H, alkyl, —Cy-alkyl, —Ph-alkyl, —Ph—O-alkyl, —Ph—CN or —Ph—F; Cy is 1,4-cyclohexylene; and Ph is 1,4-phenylene; can be used as dielectrics for electrooptical display elements.

10 Claims, No Drawings

HYDROTERPHENYLS

This is a continuation of application Ser. No. 480,199, filed Mar. 30, 1983, now abandoned.

The present invention relates to new hydroterphenyls.

SUMMARY OF THE INVENTION

It is an object of this invention to provide new stable liquid crystal compounds which are suitable as components of liquid crystal dielectrics, especially for nematic phases with a broad nematic range and low viscosity.

Upon further study of the specification and appended claims, further objects and advantages of this invention will become apparent to those skilled in the art.

These objects have been achieved by providing new hydroterphenyls of formula I $$R^1\text{—Cy—Cy—Ph—}R^2 \quad \quad I$$

wherein $R^1$ is alkyl; $R^2$ is H, F, Cl, Br, I, OH, CN, alkyl, —O-alkyl, —COOR$^3$ or —O—CO—R$^3$; $R^3$ is H, alkyl, —Cy-alkyl, —Ph-alkyl, —Ph—O-alkyl, —Ph—CN or —Ph—F; Cy is 1,4-cyclohexylene; Ph is 1,4-phenylene; and the alkyl groups each contain 1–10 C atoms.

This invention thus relates to the compounds of formula I and a process for their preparation, e.g., comprising treating a compound which corresponds to formula I but contains (a) reducible group(s) and/or additional C—C bonds instead of hydrogen atoms, with a reducing agent, or where relevant, converting the radical $R^2$ in a resulting compound of formula I into another radical $R^2$.

The invention furthermore relates to the use of the compounds of formula I as components of liquid crystal dielectrics. The invention moreover relates to liquid crystal dielectrics containing at least one compound of the formula I, and to electrooptical display elements containing such dielectrics.

DETAILED DISCUSSION

These substances can be used like similar substances, for example the compounds known from German Offenlegungsschrift No. 2,933,563, whose disclosure is incorporated by reference herein, as components of liquid crystal dielectrics, in particular for displays based on the principle of the twisted cell.

European Offenlegungsschrift No. 0,019,665 describes a very broad general formula which encompasses some of the compounds of formula I, (i.e., those wherein $R^2$ is halogen). However, nowhere in this European Offenlegungsschrift is there any disclosure from which the preparation or use of these particular compounds is obvious.

It has been found that the compounds of formula I are outstandingly suitable as components of liquid crystal dielectrics. In particular, stable liquid crystal phases with a broad nematic range and a low viscosity can be prepared using them.

In addition, because of the compounds of formula I, the range of liquid crystal substances which, from various technological viewpoints, are suitable for the preparation of nematic mixtures is, quite generally, considerably extended.

The compounds of formula I have a broad field of application. Depending on a routine choice of substituents, these compounds can be used as base materials of which liquid crystal dielectrics are predominantly composed; however, compounds of formula I can also be added to liquid crystal base materials of other classes of compounds, for example in order to reduce the viscosity of such a dielectric. The compounds of formula I, especially those wherein $R^2$ is H, Cl, Br, I, OH, CN or COOH, are furthermore suitable as intermediate products for the preparation of other substances which can be used as constituents of liquid crystal dielectrics using fully conventional methods of synthesis.

The compounds of formula I are colorless in the pure state. They form liquid crystal mesophases in a temperature range favorable for electrooptical use. Chemically, they are very stable.

In the preceding and following text, $R^1$, $R^2$, $R^3$, Cy and Ph are as defined above, unless expressly indicated otherwise.

The compounds of formula I include, for example, the preferred compounds of formula I', which corresponds to formula I but in which the radical $R^2$ is CN, —COOR$^3$, —O—CO—R$^3$, halogen or OH, and, in particular, the preferred nitriles of formula Ia, the preferred esters of formulae Ib and Ic and the preferred halogen compounds of formula Id

| | |
|---|---|
| $R_1$—Cy—Cy—Ph—CN | Ia |
| $R_1$—Cy—Cy—Ph—COOR$^3$ | Ib |
| $R_1$—Cy—Cy—Ph—O—CO—R$^3$ | Ic |
| $R_1$—Cy—Cy—Ph—Hal | Id | wherein Hal is Br or I, or, secondarily, F or Cl.

Furthermore preferred, above all, as intermediate products, are the hydroterphenyl derivatives of formulae Ie to Ig:

| | |
|---|---|
| $R_1$—Cy—Cy—Ph—OH | Ie |
| $R_1$—Cy—Cy—Ph—Br | If |
| $R_1$—Cy—Cy—Ph—I | Ig. |

In the compounds of formulae I and Ia to Ig, those stereoisomers wherein the substituents on the two 1,4-cyclohexylene radicals are in each case in the trans-position relative to one another, are preferred.

In the compounds of formula I, the alkyl or O-alkyl radicals can be straight-chained or branched. Preferably, they are straight-chained and have 2, 3, 4, 5 or 6 C atoms and accordingly are preferably ethyl, propyl, butyl, pentyl, hexyl, ethoxy, propoxy, butoxy, pentyloxy or hexyloxy, and furthermore methyl, heptyl, octyl, nonyl, decyl, methoxy, heptyloxy, octyloxy, nonyloxy or decyloxy.

Compounds of formulae I and Ia to Ig with branched end groups $R^1$ or $R^2$ can occasionally be of importance because they have a better solubility in the customary liquid crystal base materials, but especially as chiral doping substances, if they are optically active. Branched groups of this type as a rule contain not more than one chain-branching. Preferred branched radicals $R^1$ and $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-heptyl (=1-methylhexyl), 2-octyl (=1-methylheptyl), 2-ethylphenyl, isopropoxy, 2-methylpropoxy, 2-methylbutoxy, 3-methylbutoxy, 2-methylpentyloxy, 3-methylpentyloxy, 2-ethylhexyloxy, 1-methylhexyloxy and 1-methylheptyloxy.

The compounds of formula I can be prepared by methods which are known per se, and, e.g., which are described in the literature (for example in the standard works, e.g., Houben-Weyl, Methoden der Organischen Chemie [Methods of Organic Chemistry], Georg-Thieme Verlag, Stuttgart), and in particular under reaction conditions which are known and suitable for the reactions mentioned. It is also possible to utilize variants which are known per se and are not mentioned here in more detail.

If desired, the starting substances can also be formed in situ, in a manner such that they are not isolated from the reaction mixture but are immediately reacted further to give the compounds of formula I.

The compounds of formula I are preferably prepared by reducing a compound of formula II

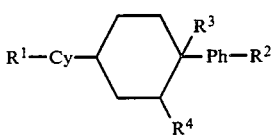

wherein either $R^3$ is OH and $R^4$ is H, or $R^3$ and $R^4$ together are a C—C bond.

The carbinols of formula II ($R^3$ is OH, $R^4$ is H) can be conventionally obtained, for example, by hydrogenation of cyclohexylphenols of the formula $R^1$—Cy—Ph—OH to give cyclohexylcyclohexanols of the formula $R^1$—Cy—Cy—OH, oxidation to give the corresponding 4-$R^1$-Cy-cyclohexanones, reaction with a Grignard compound of the formula BrMg—Ph—$R^2$ and then hydrolysis. The cyclohexenes of formula II ($R^3$ and $R^4$ together are a C—C bond) can be conventionally prepared therefrom by splitting off water, for example, with a strong acid, such as sulfuric acid or p-toluenesulfonic acid, in an inert solvent, such as benzene or toluene. The starting materials of the formula $R^1$—Cy—Ph—OH and BrMg—Ph—$R^2$ are all known or readily preparable using fully conventional methods.

The starting substances of formula II are preferably reduced to the compounds of formula I by catalytic hydrogenation at temperatures of about 0° to about 200° and under pressures of about 1 to about 200 bar in an inert solvent, for example an alcohol, e.g., methanol, ethanol or isopropanol, an ether, e.g., tetrahydrofuran (THF) or dioxane, an ester, e.g., ethyl acetate, a carboxylic acid, e.g., acetic acid, or a hydrocarbon, e.g., cyclohexane.

Preferred suitable catalysts are noble metals, e.g., Pt or Pd, which can be used in the form of oxides (PtO2 or PdO), on a support (for example Pd on charcoal, calcium carbonate or strontium carbonate) or in finely divided form (for example Pt-black).

After the reduction stage, it may be preferable to convert the resulting stereoisomer mixture into the stable trans-isomer (in relation to the cyclohexane ring obtained by hydrogenation), for example by treatment with a base, e.g., K-tert-butylate, in an inert solvent, e.g., dimethylformamide (DMF), N-methylpyrrolidone or dimethylsulfoxide, at temperatures of about 0° to about 150°.

If desired, the radical $R^2$ in a resulting compound of formula I can be converted into another radical $R^2$.

Thus, chlorination or bromination of the hydroterphenyls of formula I ($R^2$ is H) leads to chlorine or bromine compounds of formula I ($R^2$ is Cl or Br), for example using elementary chlorine or bromine in an inert solvent, e.g., diethyl ether, CCl4 or acetic acid, at temperatures of about −30° to 100°, it being possible for catalysts, e.g., iron filings, iodine or AlCl3, to be present.

Nitriles of formula Ia can be obtained by reacting these chlorine or bromine compounds with Cu2(CN)2, for example in the presence of pyridine in an inert solvent, e.g., DMF or N-methylpyrrolidone, at temperatures of 40° to 200°.

Furthermore, hydroterphenyls of formula I ($R^2$ is H) can be converted into ketones of the formula $R^1$—Cy—Cy—Ph—CO—$R^5$ by acylation with carboxylic acids of the formula HOOC—$R^5$ (wherein $R^5$ is alkyl of 1-9 C atoms) or their reactive derivatives, preferably in the presence of an acid catalyst and of an inert solvent at temperatures of about 0° to 120°. Suitable derivatives of the carboxylic acids are, above all, their anhydrides and halides, for example the corresponding acid chlorides and acid bromides. Suitable catalysts are acids, e.g., HF, H3PO4 or polyphosphoric acid, or, preferably, Lewis acids, e.g., AlCl3, AlBr3, SnCl4, ZnCl2, FeCl3, SbCl5 or BF3 or its etherate, and examples of suitable solvents are CS2, hydrocarbons, e.g., hexane, halogenated hydrocarbons, e.g., methylene chloride, nitrobenzene or tetramethylenesulfone.

The ketones metnioned can be oxidized to carboxylic acids of formula I ($R^2$ is COOH), for example with hypohalite, preferably produced in situ from bromine and a base, such as NaOH, in aqueous dioxane at temperatures of about 0° to 50°.

The carboxylic acids of formula I ($R^2$ is COOH) can be converted into the corresponding acid chlorides in the customary manner, for example with SOCl2 or PCl5 at temperatures of about 0° to 100°, and these acid chlorides can be converted into the corresponding acid amides of the formula $R^1$—Cy—Cy—Ph—CONH2 with ammonia, for example in aqueous dioxane at temperatures of about 0° to 30°.

Dehydration of these amides leads to the nitriles of formula Ia. Examples of suitable agents which split off water include inorganic acid chlorides, e.g., SOCl2, PCl3, POCl3, PCl5, SO2Cl2 and COCl2, and furthermore P2O5, P2S5, AlCl3 (for example as a double compound with NaCl) and aromatic sulfonic acids and sulfonic acid halides. This process can be carried out in the presence or absence of an inert solvent at temperatures between about 20° and 150°; examples of possible solvents are aromatic hydrocarbons, e.g., benzene, toluene or xylene, and amides, e.g., DMF.

Hydrocarbons of formula I ($R^2$ is alkyl) can be obtained, for example, by reduction of the ketones mentioned of the formula $R^1$—Cy—Cy—Ph—CO—$R^5$ by the methods of Clemmensen (with zinc, amalgamated zinc or tin and hydrochloric acid, preferably in aqueous-alcoholic solution or in a heterogeneous phase system with water/benzene or water/toluene at temperatures of about 80° to 120°) or Wolff-Kishner (with hydrazine, preferably in the presence of alkali, e.g., KOH or NaOH, in a high-boiling solvent, e.g., diethylene glycol or triethylene glycol, at temperatures of about 100° to 200°). The ketones can also be hydrogenated catalytically under the abovementioned conditions to give the hydrocarbons of formula I ($R^2$ is alkyl), preferably over a Pt or Pd catalyst at temperatures of 20° to 80

° and under normal pressure in one of the solvents mentioned, for example tetrahydrofuran.

Reaction of the ketones mentioned with hydroxylamine, for example in aqueous ethanol in the presence of a base, e.g., KOH or pyridine, at temperatures of about 20° to 100°, gives the corresponding oximes, which can be converted into the corresponding amides of the formula $R^1$—Cy—Cy—Ph—NH—CO—$R^5$ under the conditions of a Beckmann rearrangement, for example with $PCl_5$ or formic acid at temperatures of about 20° to 100°. Hydrolysis, for example with aqueous mineral acids, e.g., sulfuric acid or hydrochloric acid, at temperatures of about 20° to 150° leads to the corresponding amines of the formula $R^1$—Cy—Cy—Ph—$NH_2$. These can also be prepared by nitration of the hydrocarbons of formula I ($R^2$ is H) and subsequent reduction of the resultant nitro compounds of the formula $R^1$—Cy—Cy—Ph—$NO_2$, for example by hydrogenation under the abovementioned conditions, or by a chemical route, for example with nascent hydrogen, which can be produced with the systems Fe/HCl, Zn/NaOH, Zn/$CH_3COOH$ or Sn/HCl, or with $SnCl_2$/HCl, with $H_2S$ or sulfides or with $Na_2S_2O_4$.

Phenols of formula Ie can be obtained, for example, by diazotization of the amines and subsequent boiling. The diazotization can be carried out in the customary manner with a salt or an ester of nitrous acid (e.g., $NaNO_2$ or butyl nitrate) in an acid aqueous medium, and the resulting diazonium salt solution can then be decomposed by hydrolysis at temperatures of about 50° to 150°.

Alkoxy compounds of formula I ($R^2$ is —O-alkyl) can be obtained by alkylation of the phenols of formula If, the phenol preferably first being converted into the corresponding alkali metal phenolate, for example by treatment with NaOH, KOH, $Na_2CO_3$ or $K_2CO_3$. This phenolate can then be reacted with the corresponding alkyl halide or sulfonate or dialkylsulfate, preferably in an inert solvent, e.g., acetone, DMF or dimethylsulfoxide or an excess of aqueous or aqueous-alcoholic NaOH or KOH, at temperatures of about 20° to 100°.

Esters of formula Ib (wherein $R^3$ is other than H) and Ic can also be obtained by esterification of carboxylic acids of formula I ($R^2$ is COOH) (or their reactive derivatives) with alcohols of phenols of the formula HO—$R^3$ (or their reactive derivatives) or reaction of phenols of formula Ie (or their reactive derivatives) with carboxylic acids of the formula HOOC—$R^3$ (or their reactive derivatives).

Particularly suitable reactive derivatives of the carboxylic acids mentioned are the acid halides, above all the chlorides and bromides, and furthermore the anhydrides, for example also mixed anhydrides of the formulae $R^1$—Cy—Cy—Ph—CO—O—$COCH_3$ and $R^3$—CO—O—$COCH_3$, azides and esters, in particular alkyl esters with 1-4 C atoms in the alkyl group.

Suitable reactive derivatives of the alcohols and phenols mentioned include, in particular, the corresponding metal alcoholates or phenolates of the formulae MO—$R^3$ and $R^1$—Cy—Cy—Ph—Ph—OM in which M is one equivalent of a metal, preferably an alkali metal, e.g., Na or K.

The esterification is advantageously carried out in the presence of an inert solvent. Particularly suitable solvents include ethers, e.g., diethyl ether, di-n-butyl ether, tetrahydrofuran, dioxane or anisole, ketones, e.g., acetone, butanone or cyclohexanone, amides, e.g., DMF or phosphoric acid hexamethyltriamide, hydrocarbons, e.g., benzene, toluene or xylene, halogenohydrocarbons, e.g., carbon tetrachloride or tetrachloroethylene, and sulfoxides, e.g., dimethylsulfoxide or sulfolane. Waterimmiscible solvents can at the same time advantageously be be used for azeotropic distillation of the water formed during the esterificiation. An excess of an organic base, for example pyridine, quinoline or triethylamine, may occasionally also be used as a solvent for the esterification. The esterification can also be carried out in the absence of a solvent, for example by simply heating the components in the presence of sodium acetate. The reaction temperature is usually −50° to +250°, preferably −20° to +80°. At these temperatures, the esterification reactions have as a rule ended after 15 minutes to 48 hours.

Specifically, the reaction conditions for the esterification depend largely on the nature of the starting substances used. Thus, a free carboxylic acid is as a rule reacted with a free alcohol or phenol in the presence of a strong acid, for example a mineral acid, e.g., hydrochloric acid or sulfuric acid. A preferred reaction procedure is to react an acid anhydride or, in particular, an acid chloride with an alcohol, preferably in a basic medium, particularly important bases being alkali metal hydroxides, e.g., sodium hydroxide or potassium hydroxide, alkali metal carbonates or bicarbonates, e.g., sodium carbonate, sodium bicarbonate, potassium carbonate or potassium bicarbonate, alkali metal acetates, e.g., sodium acetate or potassium acetate, alkaline earth metal hydroxides, e.g., calcium hydroxide, and organic bases, e.g., triethylamine, pyridine, lutidine, collidine, or quinoline. A further preferred embodiment of the esterification comprises first converting the alcohol or phenol into the sodium or potassium alcoholate or phenolate, for example by treatment with ethanolic sodium hydroxide solution or potassium hydroxide solution, isolating this alcoholate or phenolate and suspending it in acetone or diethyl ether, together with sodium bicarbonate or potassium carbonate, while stirring, and adding a solution of the acid chloride or anhydride in diethyl ether, acetone or DMF to the suspension, preferably at temperatures of about −25° to +20°.

The dielectrics according to this invention comprise 2 to 15, preferably 3 to 12, components, at least one of which is a compound of formula I. The other constituents are preferably chosen from the nematic or nematogenic substances, in particular the known substances, from the classes of azoxybenzenes, benzylideneanilines, biphenyls, terphenyls, phenyl- or cyclohexyl-benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4′-bis-cyclohexylbiphenyls, phenylor cyclohexyl-pyrimidines, phenyl- or cyclohexyl-dioxanes, optionally halogenated stilbenes, benzylphenyl ethers, tolanes and substituted cinnamic acids.

The most important compounds which can be used as constituents of such liquid crystal dielectrics can be characterized by formula III $$R^6\text{—}A\text{—}G\text{—}E\text{—}R^7 \qquad \text{III}$$

wherein A and E each is a carbocyclic or heterocyclic ring system from the group comprising 1,4-disubstituted benzene and cyclohexane rings, 4,4′-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is —CH=CH—, —CH=CY—, —C≡C—, —CO—O—, —CO—S—, —CH=N—, —N(O)=N—, —CH=N(O)—, —CH$_2$—CH$_2$—, CH$_2$—O—, —CH$_2$—S—, —COO—Ph—COO— or a C—C single bond, Y is halogen, preferably chlorine, or —CN and R$^6$ and R$^7$ are alkyl, alkoxy, alkanoyloxy or alkoxycarbonyloxy with up to 18, preferably up to 8, carbon atoms, or one of these radicals can also be CN, NC, NO$_2$, CF$_3$, F, Cl or Br.

In most of the compounds, R$^6$ and R$^7$ differ, one of these radicals usually being an alkyl or alkoxy group. However, other variants of the envisaged substituents are also customary. Many such substances or mixtures thereof are commercially available.

The dielectrics according to this invention usually contain about 0.1 to 60%, preferably 2 to 25%, of one or more compounds of formula I.

The dielectrics according to this invention are prepared in a manner which is customary per se. As a rule, the components are dissolved in one another, preferably at elevated temperature.

The liquid crystal dielectrics according to this invention can be modified, by suitable additives, such that they can be used in all the types of liquid crystal display elements which have hitherto been disclosed.

Such additives are known to the expert and are described in detail in the literature. For example, conductive salts, preferably ethyl-dimethyl-dodecylammonium 4-hexyl-oxybenzoate, tetrabutylammonium tetraphenylboronate or complex salts of crown ethers (compare, for example, I. Haller et al., Mol. Cryst. Liq. Cryst. Volume 24, pages 249-258 (1973)) can be added to improve the conductivity; dichroic dyestuffs can be added to prepare colored guest/host systems; or substances can be added to modify the dielectric anisotropy, the viscosity and/or the orientation of the nematic phases. Such substances are described, for example, in German Offenlegungsschriften Nos. 2,209,127, 2,240,864, 2,321,632, 2,338,281, 2,450,088, 2,637,430, 2,853,728 and 2,902,177, all of whose disclosures are incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples and in the preceding text, all temperatures are set forth uncorrected in degrees Celsius and all parts and percentages are by weight, unless otherwise indicated.

In the examples, m.p. is the melting point and c.p. is the clear point of a liquid crystal substance.

"Customary working up" means: If necessary, water and/or an organic solvent, such as toluene, CH$_2$Cl$_2$ or CHCl$_3$ is added, the phases are separated, the organic phase is evaporated and the residue is purified by chromatography and/or crystallization.

EXAMPLE 1

A solution of 28.2 g of 1-phenyl-4-(trans-4-propylcyclohexyl)-cyclohexane [obtainable by hydrogenation of trans-1-p-hydroxyphenyl-4-propylcyclohexane over PtO$_2$ in ethyl acetate at 50° to give trans-4-(trans-4-propylcyclohexyl)-cyclohexanol, oxidation with NaOCl to give 4-(trans-4-propylcyclohexyl)-cyclohexanone, reaction with C$_6$H$_5$MgBr in tetrahydrofuran and subsequent hydrolysis to give 1-phenyl-4-(trans-4-propylcyclohexyl)-cyclohexanol and dehydration with p-toluenesulfonic acid in boiling toluene]in 350 ml of tetrahydrofuran is hydrogenated over 3 g of PdO at 40° and under 1 bar until the uptake of hydrogen ceases. The mixture is filtered, the filtrate is evaporated, the resulting cis-trans mixture is dissolved in 140 ml of DMF, 14 g of K-tert-butylate is added and the mixture is heated to 100° under N$_2$ for 24 hours. After the mixture has cooled, it is poured into water and the resulting trans-1-phenyl-4-(trans-4-propylcyclohexyl)cyclohexane is filtered off, m.p. 74°, c.p. 102°.

The following compounds are obtained analogously by hydrogenation of the corresponding cyclohexenes:

trans-1-phenyl-4-(trans-4-methylcyclohexyl)-cyclohexane trans-1-phenyl-4-(trans-4-ethylcyclohexyl)-cyclohexane trans-1-phenyl-4-(trans-4-butylcyclohexyl)-cyclohexane trans-1-phenyl-4-(trans-4-pentylcyclohexyl)-cyclohexane trans-1-phenyl-4-(trans-4-hexylcyclohexyl)-cyclohexane trans-1-phenyl-4-(trans-4-heptylcyclohexyl)-cyclohexane trans-1-phenyl-4-(trans-4-octylcyclohexyl)-cyclohexane trans-1-phenyl-4-(trans-4-nonylcyclohexyl)-cyclohexane trans-1-phenyl-4-(trans-4-decylcyclohexyl)-cyclohexane trans-1-p-fluorophenyl-4-(trans-4-ethylcyclohexyl)-cyclohexane trans-1-p-fluorophenyl-4-(trans-4-propylcyclohexyl)-cyclohexane, m.p. 80°.

trans-1-p-fluorophenyl-4-(trans-4-butylcyclohexyl)-cyclohexane trans-1-p-fluorophenyl-4-(trans-4-pentylcyclohexyl)-cyclohexane trans-1-p-fluorophenyl-4-(trans-4-hexylcyclohexyl)-cyclohexane trans-1-p-chlorophenyl-4-(trans-4-ethylcyclohexyl)-cyclohexane trans-1-p-chlorophenyl-4-(trans-4-propylcyclohexyl)-cyclohexane trans-1-p-chlorophenyl-4-(trans-4-butylcyclohexyl)-cyclohexane trans-1-p-chlorophenyl-4-(trans-4-pentylcyclohexyl)-cyclohexane trans-1-p-chlorophenyl-4-(trans-4-hexylcyclohexyl)-cyclohexane trans-1-p-bromophenyl-4-(trans-4-methylcyclohexyl)-cyclohexane trans-1-p-bromophenyl-4-(trans-4-ethylcyclohexyl)-cyclohexane trans-1-p-bromophenyl-4-(trans-4-propylcyclohexyl)-cyclohexane trans-1-p-bromophenyl-4-(trans-4-butylcyclohexyl)-cyclohexane trans-1-p-bromophenyl-4-(trans-4-pentylcyclohexyl)-cyclohexane trans-1-p-bromophenyl-4-(trans-4-hexylcyclohexyl)-cyclohexane trans-1-p-bromophenyl-4-(trans-4-heptylcyclohexyl)-cyclohexane trans-1-p-bromophenyl-4-(trans-4-octylcyclohexyl)-cyclohexane trans-1-p-bromophenyl-4-(trans-4-nonylcyclohexyl)-cyclohexane
trans-1-p-bromophenyl-4-(trans-4-decylcyclohexyl)-cyclohexane
trans-1-p-iodophenyl-4-(trans-4-ethylcyclohexyl)-cyclohexane
trans-1-p-iodophenyl-4-(trans-4-propylcyclohexyl)-cyclohexane
trans-1-p-iodophenyl-4-(trans-butylcyclohexyl)-cyclohexane
trans-1-p-iodophenyl-4-(trans-pentylcyclohexyl)-cyclohexane
trans-1-p-iodophenyl-4-(trans-hexylcyclohexyl)-cyclohexane
trans-1-p-tolyl-4-(trans-4-ethylcyclohexyl)-cyclohexane
trans-1-p-tolyl-4-(trans-4-propylcyclohexyl)-cyclohexane
trans-1-p-tolyl-4-(trans-4-butylcyclohexyl)-cyclohexane
trans-1-p-tolyl-4-(trans-4-pentylcyclohexyl)-cyclohexane
trans-1-p-tolyl-4-(trans-4-hexylcyclohexyl)-cyclohexane
trans-1-p-ethylphenyl-4-(trans-4-ethylcyclohexyl)-cyclohexane
trans-1-p-ethylphenyl-4-(trans-4-propylcyclohexyl)-cyclohexane, m.p. 33°, c.p. 162°, $\gamma_{20}$ 16 cSt.
trans-1-p-ethylphenyl-4-(trans-4-butylcyclohexyl)-cyclohexane
trans-1-p-ethylphenyl-4-(trans-4-pentylcyclohexyl)-cyclohexane
trans-1-p-ethylphenyl-4-(trans-4-hexylcyclohexyl)-cyclohexane
trans-1-p-propylphenyl-4-(trans-4-ethylcyclohexyl)-cyclohexane
trans-1-p-propylphenyl-4-(trans-4-propylcyclohexyl)-cyclohexane
trans-1-p-propylphenyl-4-(trans-4-butylcyclohexyl)-cyclohexane
trans-1-p-propylphenyl-4-(trans-4-pentylcyclohexyl)-cyclohexane
trans-1-p-propylphenyl-4-(trans-4-hexylcyclohexyl)-cyclohexane
trans-1-p-butylphenyl-4-(trans-4-ethylcyclohexyl)-cyclohexane
trans-1-p-butylphenyl-4-(trans-4-propylcyclohexyl)-cyclohexane
trans-1-p-butylphenyl-4-(trans-4-butylcyclohexyl)-cyclohexane
trans-1-p-butylphenyl-4-(trans-4-pentylcyclohexyl)-cyclohexane
trans-1-p-butylphenyl-4-(trans-4-hexylcyclohexyl)-cyclohexane
trans-1-p-pentylphenyl-4-(trans-4-ethylcyclohexyl)-cyclohexane
trans-1-p-pentylphenyl-4-(trans-4-propylcyclohexyl)-cyclohexane
trans-1-p-pentylphenyl-4-(trans-4-butylcyclohexyl)-cyclohexane
trans-1-p-pentylphenyl-4-(trans-4-pentylcyclohexyl)-cyclohexane
trans-1-p-pentylphenyl-4-(trans-4-hexylcyclohexyl)-cyclohexane
trans-1-p-hexylphenyl-4-(trans-4-ethylcyclohexyl)-cyclohexane
trans-1-p-hexylphenyl-4-(trans-4-propylcyclohexyl)-cyclohexane
trans-1-p-hexylphenyl-4-(trans-4-butylcyclohexyl)-cyclohexane
trans-1-p-hexylphenyl-4-(trans-4-pentylcyclohexyl)-cyclohexane
trans-1-p-hexylphenyl-4-(trans-4-hexylcyclohexyl)-cyclohexane
trans-1-p-methoxyphenyl-4-(trans-4-ethylcyclohexyl)-cyclohexane
trans-1-p-methoxyphenyl-4-(trans-4-propylcyclohexyl)-cyclohexane
trans-1-p-methoxyphenyl-4-(trans-4-butylcyclohexyl)-cyclohexane
trans-1-p-methoxyphenyl-4-(trans-4-pentylcyclohexyl)-cyclohexane
trans-1-p-methoxyphenyl-4-(trans-4-hexylcyclohexyl)-cyclohexane
trans-1-p-ethoxyphenyl-4-(trans-4-ethylcyclohexyl)-cyclohexane
trans-1-p-ethoxyphenyl-4-(trans-4-propylcyclohexyl)-cyclohexane
trans-1-p-ethoxyphenyl-4-(trans-4-butylcyclohexyl)-cyclohexane
trans-1-p-ethoxyphenyl-4-(trans-4-pentylcyclohexyl)-cyclohexane
trans-1-p-propoxyphenyl-4-(trans-4-hexylcyclohexyl)-cyclohexane
trans-1-p-propoxyphenyl-4-(trans-4-ethylcyclohexyl)-cyclohexane
trans-1-p-propoxyphenyl-4-(trans-4-propylcyclohexyl)-cyclohexane
trans-1-p-propoxyphenyl-4-(trans-4-butylcyclohexyl)-cyclohexane
trans-1-p-propoxyphenyl-4-(trans-4-pentylcyclohexyl)-cyclohexane
trans-1-p-propoxyphenyl-4-(trans-4-hexylcyclohexyl)-cyclohexane
trans-1-p-butoxyphenyl-4-(trans-4-ethylcyclohexyl)-cyclohexane
trans-1-p-butoxyphenyl-4-(trans-4-propylcyclohexyl)-cyclohexane
trans-1-p-butoxyphenyl-4-(trans-4-butylcyclohexyl)-cyclohexane
trans-1-p-butoxyphenyl-4-(tran$-4-pentylcyclohexyl)-cyclohexane
trans-1-p-butoxyphenyl-4-(trans-4-hexylcyclohexyl)-cyclohexane
trans-1-p-pentyloxyphenyl-4-(trans-4-ethylcyclohexyl)-cyclohexane
trans-1-p-pentyloxyphenyl-4-(trans-4-propylcyclohexyl)-cyclohexane
trans-1-p-pentyloxyphenyl-4-(trans-4-butylcyclohexyl)-cyclohexane
trans-1-p-pentyloxyphenyl-4-(trans-4-pentylcyclohexyl)-cyclohexane
trans-1-p-pentyloxyphenyl-4-(trans-4-hexylcyclohexyl)-cyclohexane
trans-1-p-hexyloxyphenyl-4-(trans-4-ethylcyclohexyl)-cyclohexane
trans-1-p-hexyloxyphenyl-4-(trans-4-propylcyclohexyl)-cyclohexane
trans-1-p-hexyloxyphenyl-4-(trans-4-butylcyclohexyl)-cyclohexane
trans-1-p-hexyloxyphenyl-4-(trans-4-pentylcyclohexyl)-cyclohexane
trans-1-p-hexyloxyphenyl-4-(trans-4-hexylcyclohexyl)-cyclohexane.

EXAMPLE 2

(a) A mixture of 28.4 g of trans-1-phenyl-4-(trans-4-propylcyclohexyl)-cyclohexane, 13.4 g of AlCl₃ and 120 ml of CH$_2$Cl$_2$ is stirred at 20° for 24 hours and is then poured into 2% hydrochloric acid. Customary working up gives p-(trans-4-(trans-4-propylcyclohexyl)-cyclo-hexyl)-acetophenone. M.p. 81°, c.p. 115°.

(b) A solution of 7 g of hydroxylammonium chloride in 115 ml of water is added to a solution of 32.6 g of p-(trans-4-(trans-4-propylcyclohexyl)-cyclohexyl)-acetophenone in 200 ml of ethanol. After a solution of 5.6 g of KOH in 10 ml of water has been added, the mixture is boiled for 2 hours, cooled and diluted with water and the p-(trans-4-(trans-4-propylcyclohexyl)-cyclohexyl)-acetophenone oxime which has precipitated is filtered off, washed with water and dried.

(c) A mixture of 34.1 g of p-(trans-4-(trans-4-propylcyclohexyl)-cyclohexyl)-acetophenone oxime and 170 ml of formic acid is boiled for 12 hours and evaoprated. The crude residue, which consists of trans-1-p-acetamidophenyl-4-(trans-4-propylcyclohexyl)-cyclohexane is boiled with 340 ml of 20% H$_2$SO$_4$ for 3 hours in order to split off the acetyl group. After the mixture has been cooled, a solution of 7 g of NaNO$_2$ in 20 ml of water is added dropwise at 0°, while stirring. Stirring is continued for 1 hour and the resulting mixture is introduced in portions, while stirring, into 300 ml of 60% H$_2$SO$_4$, which has been warmed to 130°. The mixture is cooled and the resulting trans-1-p-hydroxyphenyl-4-(trans-4-propylcyclohexyl)-cyclohexane is filtered off and recrystallized from toluene.

Analogously, via
p-(trans-4-(trans-4-ethylcyclohexyl)-cyclohexyl)-acetophenone
p-(trans-4-(trans-4-butylcyclohexyl)-cyclohexyl)-acetophenone
p-(trans-4-(trans-4-pentylcyclohexyl)-cyclohexyl)-acetophenone
p-(trans-4-(trans-4-hexylcyclohexyl)-cyclohexyl)-acetophenone
and the corresponding oximes, via
trans-1-p-acetamidophenyl-4-(trans-4-ethylcyclohexyl)-cyclohexane
trans-1-p-acctamidophenyl-4-(trans-4-butylcyclohexyl)-cyclohexane
trans-1-p-acetamidophenyl-4-(trans-4-pentylcyclohexyl)-cyclohexane
trans-1-p-acetamidophenyl-4-(trans-4-hexylcyclohexyl)-cyclohexane
and the corresponding 1-p-aminophenyl compounds, there are obtained
trans-1-p-hydroxyphenyl-4-(trans-4-ethylcyclohexyl)-cyclohexane
trans-1-p-hydroxyphenyl-4-(trans-4-butylcyclohexyl)-cyclohexane
trans-1-p-hydroxyphenyl-4-(trans-4-pentylcyclohexyl)-cyclohexane
trans-1-p-hydroxyphenyl-4-(trans-4-hexylcyclohexyl)-cyclohexane.

EXAMPLE 3

A solution of 32.6 g of p-(trans-4-(trans-4-propylcyclohexyl)-cyclohexyl)-acetophenone in 320 ml of tetrahydrofuran is hydrogenated over 5 g of 5% Pd-on-C at 40° and under normal pressure until the uptake of H$_2$ ceases. The mixture is filtered and the filtrate is evaporated to give trans-1-p-ethylphenyl-4-(trans-4-propylcyclohexyl)-cyclohexane.

EXAMPLE 4

A mixture of 32.6 g of p-(trans-4-(trans-4-propylcyclohexyl)-cyclohexyl)-acetophenone, 15 g of KOH, 25 ml of 85% hydrazine and 250 ml of diethylene glycol is warmed to 100° for 1 hour. The temperature is increased slowly until the hydrazone formed decomposes, and is boiled for another 4 hours, cooled and worked up in the customary manner to give trans-1-p-ethylphenyl-4-(trans-4-propylcyclohexyl)-cyclohexane.

EXAMPLE 5

A mixture of 36.3 g of trans-1-p-bromophenyl-4-(trans-4-propylcyclohexyl)-cyclohexane, 10 g of Cu$_2$(CN)$_2$, 120 ml of pyridine and 60 ml of N-methylpyrrolidone is heated to 160° for 2 hours. The mixture is cooled, a solution of 120 g of FeCl$_3$.6H$_2$O in 600 ml of 20% hydrochloric acid and the mixture is warmed to 70° for 1.5 hours, while stirring, and worked up in the customary manner to give trans-1-p-cyanophenyl-4-(trans-4-propylcyclohexyl)-cyclohexane, m.p. 55°, c.p. 184°.

The following compounds are obtained analogously from the corresponding bromine compounds:
trans-1-p-cyanophenyl-4-(trans-4-methylcyclohexyl)-cyclohexane
trans-1-p-cyanophenyl-4-(trans-4-ethylcyclohexyl)-cyclohexane, m.p. 76°, c.p. 195°.
trans-1-p-cyanophenyl-4-(trans-4-butylcyclohexyl)-cyclohexane
trans-1-p-cyanophenyl-4-(trans-4-pentylcyclohexyl)-cyclohexane
trans-1-p-cyanophenyl-4-(trans-4-hexylcyclohexyl)-cyclohexane
trans-1-p-cyanophenyl-4-(trans-4-heptylcyclohexyl)-cyclohexane
trans-1-p-cyanophenyl-4-(trans-4-octylcyclohexyl)-cyclohexane
trans-1-p-cyanophenyl-4-(trans-4-nonylcyclohexyl)-cyclohexane
trans-1-p-cyanophenyl-4-(trans-4-decylcyclohexyl)-cyclohexane.

EXAMPLE 6

A solution of 32.6 g of p-(trans-4-(trans-4-propylcyclohexyl)-cyclohexyl)-acetophenone in 100 ml of dioxane is added dropwise to a solution of 40 g of NaOH and 48 g of bromine in 230 ml of water at 20°, while stirring. Stirring is continued for 1 hour. A solution of 14 g of NaHSO$_3$ in 140 ml of water is added and hydrochloric acid is added until the pH is 5. Customary working up (CH$_2$Cl$_2$) gives p-(trans-4-(trans-4-propylcyclohexyl)-cyclohexyl)-benzoic acid. The crude product is boiled with 60 ml of SOCl$_2$ for 2.5 hours. After evaporation, the resulting crude acid chloride is dissolved in 430 ml of dioxane, 200 ml of 25% aqueous ammonia is added and the mixture is poured onto ice and filtered to give p-(trans-4-(trans-4-propylcyclohexyl)-cyclohexyl)-benzamide. 65 g of POCl$_3$ is added dropwise to a solution of 32.7 g of this amide in 500 ml of DMF at 50°, while stirring. After the mixture has been further stirred for 1 hour, it is poured onto ice and worked up in the customary manner (CH$_2$Cl$_2$) to give trans-1-p-cyanophenyl-4-(trans-4-propyl-cyclohexyl)-cyclohexane, m.p. 55°, c.p. 184°.

The corresponding benzamides and benzonitriles are obtained analogously via p-(trans-4-(trans-4-ethylcyclohexyl)-cyclohexyl)-benzoic acid
p-(trans-4-(trans-4-butylcyclohexyl)-cyclohexyl)-benzoic acid
p-(trans-4-(trans-4-pentylcyclohexyl)-cyclohexyl)-benzoic acid
p-(trans-4-(trans-4-hexylcyclohexyl)-cyclohexyl)-benzoic acid.

EXAMPLE 7

A mixture of 30 g of trans-1-p-hydroxyphenyl-4-(trans-4-propylcyclohexyl)-cyclohexane, 6.9 g of K$_2$CO$_3$, 25 g of hexyl iodide and 250 ml of DMF is heated to 80° for 16 hours, while stirring, and is then cooled and worked up in the customary manner. Trans-1-p-hexoxyphenyl-4-(trans-4-propylcyclohexyl)-cyclohexane is obtained.

EXAMPLE 8

8 g of acetyl chloride is added to a solution of 30 g of trans-1-p-hydroxyphenyl-4-(trans-4-propylcyclohexyl)-cyclohexane and 20 ml of pyridine in 300 ml of toluene and the mixture is warmed to 80° for 1 hour. After cooling and customary working up, trans-1-p-acetoxyphenyl-4-(trans-4-propylcyclohexyl)-cyclohexane is obtained.

The following compounds are obtained analogously by esterification
trans-1-p-acetoxyphenyl-4-(trans-4-ethylcyclohexyl)-cyclohexane
trans-1-p-formyloxyphenyl-4-(trans-4-propylcyclohexyl)-cyclohexane
trans-1-p-propionyloxyphenyl-4-(trans-4-propylcyclohexyl)-cyclohexane
trans-1-p-butyryloxyphenyl-4-(trans-4-propylcyclohexyl)-cyclohexane
trans-1-p-pentanoyloxyphenyl-4-(trans-4-propylcyclohexyl)-cyclohexane
trans-1-p-hexanoyloxyphenyl-4-(trans-4-propylcyclohexyl)-cyclohexane
trans-1-p-decanoyloxyphenyl-4-(trans-4-propylcyclohexyl)-cyclohexane
trans-1-p-(trans-4-propylcyclohexylcarbonyloxy)-phenyl-4-(trans-4-propylcyclohexyl)-cyclohexane
trans-1-p-(trans-4-butylcyclohexylcarbonyloxy)-phenyl-4-(trans-4-propylcyclohexyl)-cyclohexane
trans-1-p-(trans-4-pentylcyclohexylcarbonyloxy)-phenyl-4-(trans-4-propylcyclohexyl)-cyclohexane
trans-1-p-(p-ethylbenzoyloxy)-phenyl-4-(trans-4-propylcyclohexyl)-cyclohexane
trans-1-p-(p-propylbenzoyloxy)-phenyl-4-(trans-4-propylcyclohexyl)-cyclohexane
trans-1-p-(p-butylbenzoyloxy)-phenyl-4-(trans-4-propylcyclohexyl)-cyclohexane
trans-1-p-(p-methoxybenzoyloxy)-phenyl-4-(trans-4-propylcyclohexyl)-cyclohexane
trans-1-p-(p-ethoxybenzoyloxy)-phenyl-4-(trans-4-propylcyclohexyl)-cyclohexane
trans-1-p-(p-propoxybenzoyloxy)-phenyl-4-(trans-4-propylcyclohexyl)-cyclohexane
trans-1-p-(p-cyanobenzoyloxy)-phenyl-4-(trans-4-propylcyclohexyl)-cyclohexane.

EXAMPLE 9

32.8 g of p-(trans-4-(trans-4-propylcyclohexyl)-cyclohexyl)-benzoic acid is boiled with 24 g of SOCl$_2$ for 1 hour. The mixture is evaporated, the resulting crude acid chloride is dissolved in 150 ml of toluene, and 8 g of pyridine and 6 g of propanol are added and the mixture is boiled for 2 hours. Cooling and customary working up (CH$_2$Cl$_2$) give propyl p-(trans-4-(trans-4-propylcyclohexyl)-cyclohexyl)-benzoate.

The following compounds are obtained analogously by esterification:
methyl p-(trans-4-(trans-4-ethylcyclohexyl)-cyclohexyl)-benzoate
ethyl p-(trans-4-(trans-4-ethylcyclohexyl)-cyclohexyl)-benzoate
propyl p-(trans-4-(trans-4-ethylcyclohexyl)-cyclohexyl)-benzoate
butyl p-(trans-4-(trans-4-ethylcyclohexyl)-cyclohexyl)-benzoate
pentyl p-(trans-4-(trans-4-ethylcyclohexyl)-cyclohexyl)-benzoate
hexyl p-(trans-4-(trans-4-ethylcyclohexyl)-cyclohexyl)-benzoate
p-cyanophenyl p-(trans-4-(trans-4-ethylcyclohexyl)-cyclohexyl)-benzoate
methyl p-(trans-4-(trans-4-propylcyclohexyl)-cyclohexyl)-benzoate
ethyl p-(trans-4-(trans-4-propylcyclohexyl)-cyclohexyl)-benzoate
butyl p-(trans-4-(trans-4-propylcyclohexyl)-cyclohexyl)-benzoate
pentyl p-(trans-4-(trans-4-propylcyclohexyl)-cyclohexyl)-benzoate
hexyl p-(trans-4-(trans-4-propylcyclohexyl)-cyclohexyl)-benzoate
heptyl p-(trans-4-(trans-4-propylcyclohexyl)-cyclohexyl)-benzoate
octyl p-(trans-4-(trans-4-propylcyclohexyl)-cyclohexyl)-benzoate
nonyl p-(trans-4-(trans-4-propylcyclohexyl)-cyclohexyl)-benzoate
decyl p-(trans-4-(trans-4-propylcyclohexyl)-cyclohexyl)-benzoate
trans-4-propylcyclohexyl p-(trans-4-(trans-4-propylcyclohexyl)-cycLohexyl)-benzoate
trans-4-butylcyclohexyl p-(trans-4-(trans-4-propylcyclohexyl)-cyclohexyl)-benzoate
trans-4-pentylcyclohexyl p-(trans-4-(trans-4-propylcyclohexyl)-cyclohexyl)-benzoate
p-tolyl p-(trans-4-(trans-4-propylcyclohexyl)-cyclohexyl)-benzoate
p-propylphenyl p-(trans-4-(trans-4-propylcyclohexyl)-cyclohexyl)-benzoate
p-butylphenyl p-(trans-4-(trans-4-propylcyclohexyl)-cyclohexyl)-benzoate
p-pentylphenyl p-(trans-4-(trans-4-propylcyclohexyl)-cyclohexyl)-benzoate
p-methoxyphenyl p-(trans-4-(trans-4-propylcyclohexyl)-cyclohexyl)-benzoate
p-ethoxyphenyl p-(trans-4-(trans-4-propylcyclohexyl)-cyclohexyl)-benzoate
p-decyloxyphenyl p-(trans-4-(trans-4-propylcyclohexyl)-cyclohexyl)-benzoate
p-cyanophenyl p-(trans-4-(trans-4-propylcyclohexyl)-cyclohexyl)-benzoate
propyl p-(trans-4-(trans-4-butylcyclohexyl)-cyclohexyl)-benzoate
butyl p-(trans-4-(trans-4-butylcyclohexyl)-cyclohexyl)-benzoate
pentyl p-(trans-4-(trans-4-butylcyclohexyl)-cyclohexyl)-benzoate
p-cyanophenyl p-(trans-4-(trans-4-butylcyclohexyl)-cyclohexyl)-benzoate propyl p-(trans-4-(trans-4-pentylcyclohexyl)-cyclohexyl)-benzoate butyl p-(trans-4-(trans-4-pentylcyclohexyl)-cyclohexyl)-benzoate pentyl p-(trans-4-(trans-4-pentylcyclohexyl)-cyclohexyl)-benzoate p-cyanophenyl p-(trans-4-(trans-4-pentylcyclohexyl)-cyclohexyl)-benzoate propyl p-(trans-4-(trans-4-hexylcyclohexyl)-cyclohexyl)-benzoate butyl p-(trans-4-(trans-4-hexylcyclohexyl)-cyclohexyl)-benzoate pentyl p-(trans-4-(trans-4-hexylcyclohexyl)-cyclohexyl)-benzoate p-cyanophenyl p-(trans-4-(trans-4-hexylcyclohexyl)-cyclohexyl)-benzoate.

The examples which follow are of dielectrics according to the invention containing at least one compound of the formula I:

EXAMPLE A

A mixture of

21% of p-(trans-4-propylcyclohexyl)-benzonitrile,

30% of p-(trans-4-pentylcyclohexyl)-benzonitrile,

22% of p-(trans-4-heptylcyclohexyl)-benzonitrile,

12% of trans-1-p-cyanophenyl-4-(trans-4-ethylcyclohexyl)-cyclohexane and

15% of trans-1-p-cyanophenyl-4-(trans-4-propylcyclohexyl)-cyclohexane has an m.p. of −12° and a c.p. of 82°.

The mixture can be used, for example, for a "twisted nematic display (TND)" for "static drive" ("direct drive") with operating voltages of 3–10 volts.

EXAMPLE B

A mixture of

20% of p-(trans-4-ethylcyclohexyl)-benzonitrile,

13% of 4-ethyl-4'-cyanobiphenyl,

2% of 4-butyl-4'-cyanobiphenyl,

9% of p-cyanophenyl p-ethylbenzoate,

6% of p-cyanophenyl p-propylbenzoate,

13% of trans-1-p-cyanophenyl-4-(trans-4-ethylcyclohexyl)-cyclohexane and

17% of trans-1-cyanophenyl-4-(trans-4-propylcyclohexyl)-cyclohexane has an m.p. of −8° and a c.p. of 64°.

This mixture can be used, for example for a TND at low operating voltages.

EXAMPLE C

A mixture of

12% of p-(trans-4-propylcyclohexyl)-benzonitrile,

10% of p-(trans-4-butylcyclohexyl)-benzonitrile,

19% of p-(trans-4-pentylcyclohexyl)-benzonitrile,

10% of p-(trans-4-heptylcyclohexyl)-benzonitrile,

12% of 4-cyano-4'-(trans-4-pentylcyclohexyl)-biphenyl,

12% of trans-1-p-cyanophenyl-4-(trans-4-ethylcyclohexyl)-cyclohexane,

15% of trans-1-p-cyanophenyl-4-(trans-4-propylcyclohexyl)-cyclohexane and

10% of trans-1-p-fluorophenyl-4-(trans-4-propylcyclohexyl)-cyclohexane has an m.p. of −13° and a c.p. of 97°.

It is suitable, for example, as a nematic solvent for dichroic dyestuffs ("host mixture").

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A hydroterphenyl of the formula

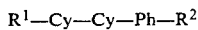

$$R^1-Cy-Cy-Ph-R^2$$

wherein $R^1$ is alkyl; $R^2$ is $-COOR^3$ or $-O-CO-R^3$; $R^3$ is H, alkyl, $-Cy$-alkyl, $-Ph$-alkyl, $-Ph-O$-alkyl, $-Ph-CN$ or $-Ph-F$; Cy is 1,4-cyclohexylene; Ph is 1,4-phenylene; and all alkyl groups each independently contain 1–10 C atoms.

2. A compound of claim 1 wherein $R^2$ is $-COOR^3$.

3. A compound of claim 1 wherein $R^2$ is $-O-CO-R^3$.

4. A compound of claim 1 wherein the substituents on each Cy group are in the trans-position relative to each other.

5. A compound of claim 1 wherein all alkyl groups are straight chained.

6. A compound of claim 5 wherein each alkyl group is of 2–6 C-atoms.

7. A liquid crystal dielectric useful in electrooptical display elements, comprising at least two liquid crystalline components, wherein at least one such component is a hydroterphenyl of claim 1.

8. A liquid crystal dielectric of claim 7 comprising 2–15 components.

9. A liquid crystal dielectric of claim 7 wherein the amount of said hydroterphenyl components is 0.1 to 60 wt. %.

10. In an electrooptical display element, based on an electrooptical cell comprising a liquid crystal dielectric, the improvement wherein the dielectric is that of claim 7.

* * * * *